(12) United States Patent
Geisler

(10) Patent No.: US 6,231,610 B1
(45) Date of Patent: May 15, 2001

(54) ANTERIOR CERVICAL COLUMN SUPPORT DEVICE

(75) Inventor: Fred Geisler, Evanston, IL (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

(21) Appl. No.: 09/382,808

(22) Filed: Aug. 25, 1999

(51) Int. Cl.[7] ........................................ A61F 2/44
(52) U.S. Cl. ............................................. 623/17.11
(58) Field of Search .................... 623/17.11, 17.16; 606/61

(56) References Cited

U.S. PATENT DOCUMENTS

| | | |
|---|---|---|
| 4,834,757 | 5/1989 | Brantigan . |
| 5,425,772 * | 6/1995 | Brantigan ..................... 623/17.11 |
| 5,609,635 * | 3/1997 | Michelson . |
| 5,766,196 | 7/1998 | Matsuzaki et al. . |
| 5,766,252 | 6/1998 | Henry et al. . |
| 5,865,845 | 2/1999 | Thalgott . |
| 6,066,175 * | 5/2000 | Henderson et al. ............ 623/17.11 |

* cited by examiner

Primary Examiner—Jeffrey A. Smith
(74) Attorney, Agent, or Firm—Donald O. Nickey; Andrew G. Rozycki

(57) ABSTRACT

An spinal column support device for stabilizing and repairing problems associated with the material located between vertebra located in the cervical area of the spinal column. The support device has a hollow isosceles trapezoidal right prism-shaped skeletal frame with two load bearing surfaces. Each load bearing surface includes serrations. The support device also includes a cervical plate having two screw holes. The support devices is inserted between two vertebrae located in the cervical area of the spine wherein each vertebrae rests on a load bearing surface. The serrations keep the support device from backing out, while screws in the screw holes of the cervical plate help hold the cervical plate in position.

7 Claims, 2 Drawing Sheets

ANTERIOR CERVICAL COLUMN SUPPORT DEVICE

BACKGROUND OF THE INVENTION

1. Field of the Invention

The present invention relates to spinal column spacers and specifically to an anterior cervical column support device.

2. Description of the Prior Art

Several prior art spacers exist for repairing the spinal column. However, most spacers are designed for the lumbar or thoracic regions of the spine whereas most devices for repairing the cervical area of the spine usually involves some type of screw and rod system. The following U.S. Patents are examples.

U.S. Pat. No. 5,397,363 issued to Gelbard on Mar. 14, 1995 shows a spinal stabilization implant system. It uses plates and screws to stabilize the vertebrae of the cervical area. "The instant invention is a surgical implant system for the stabilization of the human spine by fixation of the vertebra. The system is based upon screws, nuts, rods, hooks, cross-members and variations thereof. The preferred embodiment employs a metal screw for placement in the sacrum or pedicle defined by a coarse self-tapping thread and a U-shaped saddle for placement of conventional alignment rods. Unique to this invention is that the screw is threaded on the outer surface of the saddle allowing the alignment rod to be securely fastened into the saddle by placement of the rod therein and the fastening of a nut to the top of the saddle. Further unique to this invention is the use of an elongated sagittal traverse support member that can accommodate the saddle protrusion either in a fixed position or by use of a rotatable insert that allows the cross member to be tightly fastened to the saddle in a variable alignment. The top-loading attachment is further applicable to caudal, cranial, and the like hook components. An anterior cervical plate is set forth using a second plate to permanently lock the cervical plate in position. The second plate does not rely upon the bone to support the place thus providing means to prevent any bone attachment screws from loosening or otherwise backing out of the bone."

U.S. Pat. No. 5,507,745 issued to Logroscrino et al. on Apr. 16, 1996 shows an occipito-cervical osteosynthesis instrumentation. It is another example of a rod-type system used on the cervical area of the spine. It comprises "two separate similar parts, namely a right and a left part, each formed by a cervical rod having asperities and an elongate occipital plate which forms one piece with said rod and extends said rod toward the occiput in the position of use, [an] adjustable means for anchoring the rod to the vertebrae and the plate to the occiput, each part being so preangulated and shaped as to be adapted to the anatomy of the occipito-cervical connection." This patent also recognizes that the cervical area of the spine requires a specific curvature for proper healing.

U.S. Pat. No. 5,713,900 issued to Benzel et al. on Feb. 3, 1998 shows an apparatus for retaining bone portions in a desired spatial relationship. The abstract states that it is "[a] apparatus for retaining first and second bone portions in a desired spatial relationship compris[ing] a first member positionable along the first and second bone portions. A second member connectable with the first bone portion has surface member defining an opening. A fastener is extendable through the opening in the second member to connect the second member to the first bone portion. The fastener has a first portion for engaging the first bone portion and a second portion for clamping the first member against the second member to fix the first and second members against relative movement. The first member is also connected to the second bone portion."

Very few references disclose the use of implantable spacers as a solution to cervical vertebra stabilization. Those that do, lack the advantages of the present invention.

The human spinal column consists of 33 (sometimes 34) vertebrae divided into five groups: cervical, thoracic, lumbar, sacral and coccygeal vertebrae areas. The sacral vertebrae are fused into a single bone as is the coccygeal vertebrae, usually designated as the coccyx. The movable vertebrae are found in the cervical, thoracic and lumbar areas. Each area has a characteristic curve. Various vertebrae differ in size and shape depending on the location in the spinal column. This means that a spacer designed for the lumbar or thoracic region will not perform properly in the cervical region. The present invention solves the problem of stabilization of the cervical vertebrae by providing a properly designed spacer for the cervical area.

SUMMARY OF THE INVENTION

It is an object of the present invention to provide an implantable spacer which performs as an anterior cervical column support device.

The instant invention is an anterior cervical spinal column support. It consists of a hollow isosceles trapezoidal right prism-shaped skeletal frame designed to fit between and stabilize cervical vertebrae. It provides spacing and support where, for example, the intevertebral disc has failed due to a slipped, herniated or ruptured disc. Specifically, it is used in one or two level anterior cervical discectomy in degenerative disc disease where. fusion and internal stabilization is desired. It also corrects and provides better support for the lateral bending and lordosis angles. It includes bottom and top load bearing surfaces. Each surface lies in a plane which makes a 1–5 (preferably 1–2) degree angle with the horizon so as to provide the proper angle for the cervical vertebrae. These surfaces bear the weight and forces on the vertebrae and are held in place primarily by frictional forces between the vertebrae and the serrated portions on the top and bottom load bearing surfaces. The support also includes a plate attached to the back portion and including screw holes allowing the plate to be connect to the vertebrae by screws. These screws do not provide primary support and are not load bearing. Their function is to hold the plate in position. The support is constructed of any bio-compatible material, such as titanium. The hollow space within the support is designed to hold a bone graft, or any other type of bone grafting material.

It is an object of the present invention to provide an inter-discal spacer and support for the vertebrae of the cervical area of the spine.

It is an object of the present invention to provide a cervical inter-discal support which includes a hollow portion for receiving bone grafting material.

It is an object of the present invention to provide an anterior cervical column support device which restores and/or maintains the correct lordodic balance better than prior art rod and screw devices.

It is an object of the present invention to provide an anterior cervical column support device which properly restores saggital balance.

These together with other objects of the invention, along with various features of novelty which characterize the invention, are pointed out with particularity in the claims annexed to and forming part of this disclosure. For a better understanding of the invention, its operating advantages and the specific objects attained by its uses, reference should be made to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
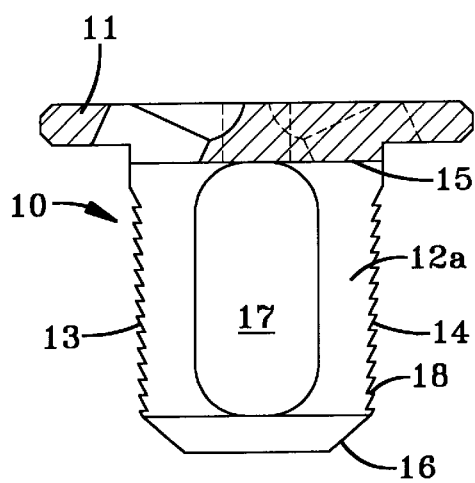
FIG. 1 is a side view of the anterior cervical column support device.

The anterior cervical column support device 10 is a hollow isosceles trapezoidal right prism-shaped skeletal frame comprising a rear plate 11, two trapezoidal shaped side surfaces 12a and 12b, a rectangular shaped top load bearing surface 13, a rectangular shaped bottom load bearing surface 14, a back surface 15 and a front surface 16. The rear plate 11 is attached to the back surface 15 of the support device 10. The rear plate 11 also includes two screw holes for attaching the plate to the two adjacent vertebral bodies on either side of the support device 10 once the support device 10 is in place. The width "W" of the back surface 15 and the front surface 16 are equal. The height "A" of the front surface 16, however, is shorter than the height "B" of the back surface 15. This configuration forms the isosceles trapezoidal shape. The top load bearing surface 13, bottom load bearing surface 14 and the two side surfaces 12a and 12b are skeletal in configuration. Each of these surfaces provide access to the interior 17 of the support device 10. The interior 17 of the support device 10 receives cartilage or any other bone grafting material. This allows the vertebrae on each side of the support device 10 to fuse together using the cartilage material.

As shown in FIG. 1, the side view of the anterior cervical column support device 10 shows the rear plate 11 attached to the back surface 15 of the support device 10. It also shows a side surface 12a. Each side surface 12a and 12b has the same shape and size. FIG. 1 also shows a side view of the top load bearing surface 13 and the bottom load bearing surface 14. These surfaces 13 and 14 have the same size and shape and are named differently for the purpose of description only. Each surface 13 and 14 includes serrations 18.

Figure 2:
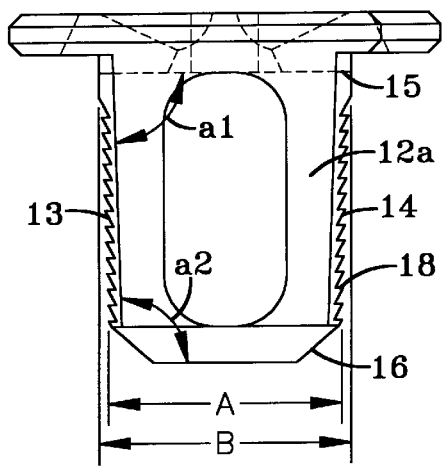
FIG. 2 is a side view of the anterior cervical column support device showing details of the angles between the top load bearing surface and the bottom load bearing surface.

FIG. 2 shows a detailed side view of the anterior cervical column support device 10. It shows the height "B" of the rear surface 15 and the height "A" of the front surface 16. The side surfaces 12a and 12b have a trapezoidal shape which can clearly be seen from FIG. 2. The back end of the trapezoid has a height "B" and the front end of the trapezoid has a height "A." Height "A" and height "B" are designed for specific areas within the cervical region of the spine and specifically are designed to fit between certain vertebrae in that area. The heights "A" and "B" provide the proper spacing between the vertebra while the difference between the heights "A" and "B" create an angle a1 between the rear surface 15 and the top load bearing surface 13 and an angle a2 between the front surface 16 and the top load bearing surface 13. Angle a1 can be between 85 and 89 degrees whereas the corresponding angle a2 is between 91 and 95 degrees. In the preferred embodiment, angle a1 is between 88 and 89 degrees whereas angle a2 is between 91 and 92 degrees. Angles a1 and a2 are also present with respect to the bottom load bearing surface 14 as it is attached to the rear surface 15 and the front surface 16. The angles a1 and a2, the top load bearing surface 13 and the bottom load bearing surface 14 form a trapezoidal shape which holds the vertebrae in the proper position. In this manner, the support device 10 holds the proper lordodic balance and restores the sagittal balance between the vertebrae in the cervical area of the spine.

Figure 3:
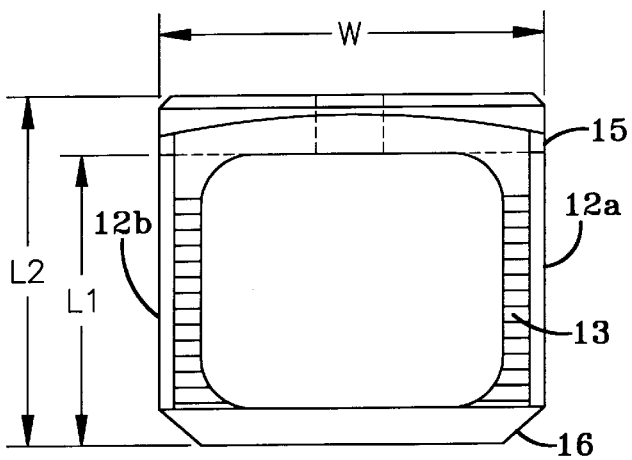
FIG. 3 is a top view of the anterior cervical column support device showing the serrations on the top load bearing surface of the support device.

FIG. 3 shows a top view of the anterior cervical support device 10. The serrations 18 on the top load bearing surface 13 are clearly visible as is the rectangular shape of the top load bearing surface 13. The width "W" of the top load bearing surface 13, the bottom load bearing surface 14, the rear surface 15 and the front surface 16 are all equal. In the preferred embodiment, the width is 12 to 15 millimeters. However, this width can vary according to the size of the vertebrae of the cervical area of the spine of the particular patient.

Figure 4:
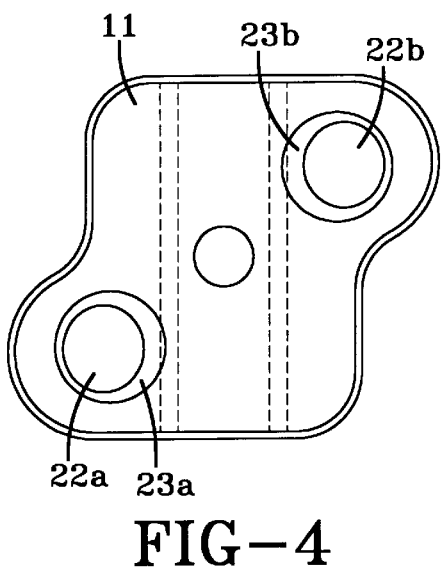
FIG. 4 is a rear view of the anterior cervical column support device showing the rear plate and associated screw holes.

FIG. 4 shows a detailed view of the rear plate 11. The rear plate 11 is primarily a cervical plate used in the prior art. The rear plate 11 is attached to the rear surface 15 of the anterior cervical column support device 10. The rear plate 11 includes two screw holes 22a and 22b. These screw holes 22a and 22b include angled indentations 23a and 23b which make one screw go into the vertebra supported by the top load bearing surface 13 and the other screw go into the vertebra supported by the bottom load bearing surface 14. The screws (not shown in the drawings) can be made of any bio-compatible material. Preferably, the screws are titanium uni-cortical screws having a 14 millimeter length. These screws are used to hold the rear plate 11 in position.

All components of the anterior cervical column support device are made of biocompatible material. Preferably the material is titanium, 6AL-4V ELI alloy.

Figure 5:
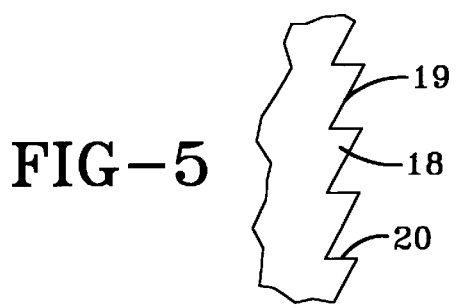
FIG. 5 is a detailed side view of top load bearing surface showing the serrations.
Figure 6:
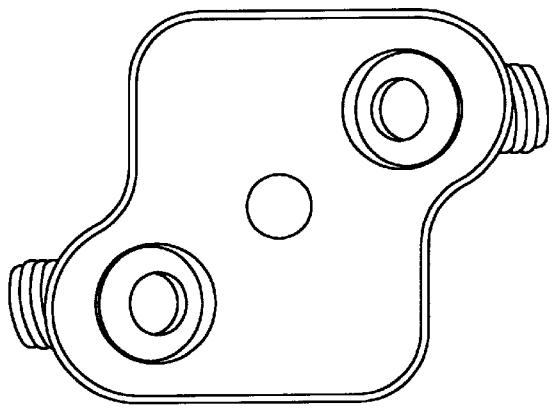
FIG. 6 is a rear view of the anterior cervical column support device showing the rear plate with the associated screws.
Figure 7:
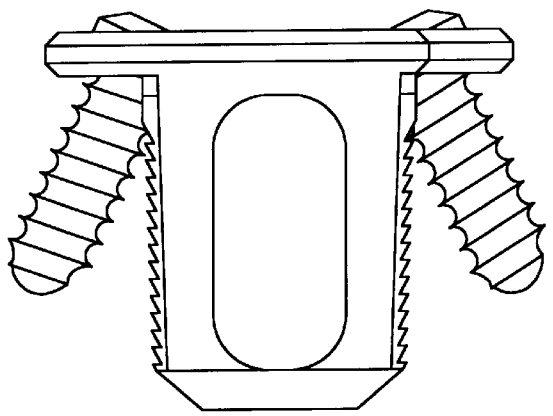
FIG. 7 is a side view of the anterior cervical column support device with the associated screws.
Figure 8:
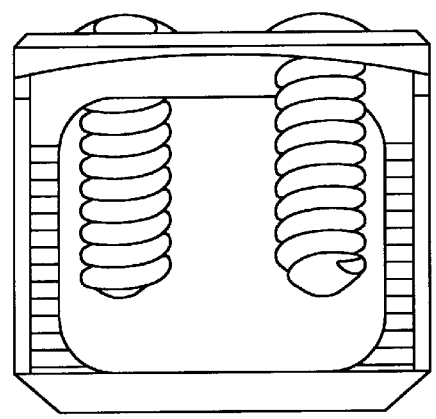
FIG. 8 is a top view of the anterior cervical column support device with the associated screws.

A detailed view of these serrations 18 can be seen in FIG. 5. Arrow 21 in FIG. 5 indicates the direction of insertion of the support device 10. With respect to the direction of insertion, the serrations 18 include a sloping front side 19 and a perpendicular 20 rear side. This allows for easy movement in one direction and difficult movement in the other direction. These serrations 18 provide the primary frictional support for the support device 10.

It will be apparent to those skilled in the art that various modifications and variations can be made to the anterior cervical spinal column support device. Thus, it is intended that the present invention cover such modifications and variations, provided they come within the scope of the appended claims and their equivalents. The disclosure of all publications cited above are expressly incorporated herein by reference in their entireties to the same extent as if each were incorporated by reference individually.

I claim:

1. A anterior cervical column support device for insertion between a first spinal vertebra and a second spinal vertebra, comprising:

a hollow isosceles trapezoidal right prism-shaped skeletal frame having a front surface, a rear surface, two side surfaces, a top load bearing surface and a bottom load bearing surface;

each side surface has a trapezoidal shape and attached between the front surface and rear surface;

the top load bearing surface attaches to each side surface and to the front and rear surfaces such that an obtuse angle is formed between the top load bearing surface and the front surface and an acute angle is formed between the top load bearing surface and the rear surface, wherein the top load bearing surface includes serrations for increasing frictional forces between the top load bearing surface and the first vertebrae; and the bottom load bearing surface attaches to each side surface and to the front and rear surfaces such that an obtuse angle is formed between the bottom load bearing surface and the front surface and an acute angle is formed between the bottom load bearing surface and the rear surface, wherein the bottom load bearing surface includes serrations for increasing frictional forces between the bottom load bearing surface and the second vertebrae; and a rear plate attached to the rear surface of the support device, the rear plate including two indented offset screw holes for receiving two screws for holding the rear plate in position.

2. The anterior cervical column support device of claim 1 wherein the acute angle between the top load bearing surface and the rear surface and the acute angle between the bottom load bearing surface and the rear surface is between 85 and 89 degrees and the corresponding obtuse angle between the top load bearing surface and the front surface and the obtuse angle between the bottom load bearing surface and the front surface is between 91 and 95 degrees.

3. The anterior cervical column support device of claim 2 wherein the acute angle between the top load bearing surface and the rear surface and the acute angle between the bottom load bearing surface and the rear surface is between 88 and 89 degrees and the corresponding obtuse angle between the top load bearing surface and the front surface and the obtuse angle between the bottom load bearing surface and the front surface is between 91 and 92 degrees.

4. The anterior cervical column support device of claim 1 wherein one screw is driven into the first vertebrae and one screw is driven into the second vertebrae.

5. The anterior cervical column support device of claim 1 wherein the entire support device is constructed of bio-compatible material.

6. The anterior cervical column support device of claim 5 wherein the bio-compatible material is titanium.

7. The anterior cervical column support device of claim 1 wherein the serrations on the top load bearing surface and the serrations on the bottom load bearing surface are uni-directional.

* * * * *